(12) United States Patent
Pini et al.

(10) Patent No.: US 11,519,843 B2
(45) Date of Patent: Dec. 6, 2022

(54) BIOSENSOR PLATFORM AND METHOD FOR THE SIMULTANEOUS, MULTIPLEXED, ULTRA-SENSITIVE AND HIGH THROUGHPUT OPTICAL DETECTION OF BIOMARKERS

(71) Applicant: MECWINS, S.A., Tres Cantos (ES)

(72) Inventors: Valerio Pini, Madrid (ES); Andreas Thon, Madrid (ES); Antonio Salvador-Matar Renteria, Madrid (ES); Virginia Cebrián Hernando, Madrid (ES); Carlos García Aguado, Madrid (ES); Jesús Oscar Ahumada Heredero, Madrid (ES)

(73) Assignee: MECWINS, S.A., Madrid (ES)

( * ) Notice: Subject to any disclaimer, the term of this patent is extended or adjusted under 35 U.S.C. 154(b) by 356 days.

(21) Appl. No.: 16/839,138

(22) Filed: Apr. 3, 2020

(65) Prior Publication Data
US 2020/0319085 A1     Oct. 8, 2020

(30) Foreign Application Priority Data
Apr. 3, 2019     (EP) .................................. 19382244

(51) Int. Cl.
*G01N 15/14*     (2006.01)
*G01N 15/06*     (2006.01)
(Continued)

(52) U.S. Cl.
CPC ......... *G01N 15/1468* (2013.01); *G01N 15/06* (2013.01); *G01N 33/54346* (2013.01);
(Continued)

(58) Field of Classification Search
CPC .............. G01N 15/06; G01N 15/1468; G01N 2015/0065; G01N 33/54346;
(Continued)

(56) References Cited

U.S. PATENT DOCUMENTS 10,989,724 B1 *   4/2021   Holmes ................. G01N 15/14
11,060,976 B2 *   7/2021   Zheng ................... G01N 21/01
(Continued)

OTHER PUBLICATIONS

European search report for EP19382244.2, dated Sep. 30, 2019, 2 pages.

*Primary Examiner* — Tri T Ton
(74) *Attorney, Agent, or Firm* — Danielson Legal LLC

(57) ABSTRACT

Biosensing platform for simultaneous, multiplexed, high throughput and ultra-sensitive optical detection of biomarkers labelled with plasmonic nanoparticles, the platform being provided with a biosensor, a broadband and continuous spectrum illumination source, an optical detector for simultaneously capturing spatially resolved and spectrally resolved the scattering signal of each individual nanoparticle, an autofocus system and an optical system adapted to collect the scattered signal of the biosensor's surface onto the optical detector, the platform being provided with translation means for the optical system and/or the biosensor, such that the optical system and the biosensor can be displaced relative to each other in the three dimensions, and wherein the processing means are adapted to: i) simultaneously capture spatially and spectrally resolved scattering signals from each nanoparticle individually, and ii) to analyze these signals simultaneously with the capture process.

8 Claims, 6 Drawing Sheets

(51) Int. Cl.
*G01N 33/543* (2006.01)
*G01N 15/00* (2006.01)

(52) U.S. Cl.
CPC ............... *G01N 2015/0065* (2013.01); *G01N 2015/0693* (2013.01); *G01N 2015/1472* (2013.01); *G01N 2015/1486* (2013.01); *G01N 2015/1493* (2013.01); *G01N 2015/1497* (2013.01)

(58) Field of Classification Search
CPC .............. G01N 2015/0693; G01N 2015/1472; G01N 2015/1486; G01N 2015/1493; G01N 2015/1497; G01N 21/554; G01N 33/5436; G01N 33/587; G01J 2003/2806; G01J 2003/2826; G01J 3/2823; G02B 21/0004
USPC ......................................................... 436/518
See application file for complete search history.

(56) References Cited

U.S. PATENT DOCUMENTS

| | | | |
|---|---|---|---|
| 2004/0218184 A1* | 11/2004 | Jorgenson | G01N 15/147 356/419 |
| 2005/0244863 A1* | 11/2005 | Mir | B82Y 5/00 435/7.1 |
| 2008/0137080 A1 | 6/2008 | Bodzin | |
| 2013/0176617 A1 | 7/2013 | Tamura | |
| 2016/0103308 A1 | 4/2016 | Furuya | |
| 2019/0022944 A1* | 1/2019 | Döhler | B33Y 50/00 |

\* cited by examiner

BIOSENSOR PLATFORM AND METHOD FOR THE SIMULTANEOUS, MULTIPLEXED, ULTRA-SENSITIVE AND HIGH THROUGHPUT OPTICAL DETECTION OF BIOMARKERS

CROSS-REFERENCE TO RELATED APPLICATIONS

The present application claims the benefit of and priority to European Patent Application No. 19382244.2, filed on Apr. 3, 2019, the entire disclosure of which is incorporated by reference as if set forth in its entirety herein.

BACKGROUND OF THE INVENTION

Field of the Invention

The present invention relates to multiplexed biosensors for diagnostic applications that detect and quantify the physical changes that a biological recognition layer bound to a solid transducer undergoes when it interacts with a sample containing target molecules.

Description of the Related Art

Biosensors use the capacity of some biomolecules (receptors) to specifically bind to (recognize) complementary biomolecules (ligands). The most typical interactions are complementary nucleic acid hybridization and antibody/antigen binding. Biosensors are increasingly sought after in fundamental biological studies, health sciences research, drug discovery and clinical diagnosis. Depending on the measured physical change, biosensors can be classified as electrochemical, mechanical and optical biosensors. In EP3153844 a new biosensing platform is presented for the ultra-sensitive detection of protein biomarkers deposited onto a surface. The key features of this biosensing platform are:

1) Each biomarker is labeled with a specific type of plasmonic nanoparticle (nanospheres, nanorods, nanocubes, nanoprisms, etc.)

2) Plasmonic nanoparticles are deposited onto a functionalized suspended multidielectric substrate that allows at the same time to strongly enhance the weak scattering signal coming from plasmonic nanoparticles (optoplasmonic effect) and to weigh the mass of the nanoparticles.

The biosensing platform presents a dual transduction mechanism based on optical detection, plasmonic nanoparticles are optically detected with standard dark-field microscopy, and on mechanical detection, the mass of the plasmonic nanoparticles is detected by measuring the change of the resonance frequency of the suspended mechanical substrate after the deposition of the nanoparticles.

This biosensing platform is very robust and has been tested with infectious, inflammatory and oncologic protein biomarkers, and it presents ultra-high detection sensitivity, up to six orders of magnitude better than the standard in routine clinical practice. However, the main drawbacks of this known biosensing platform are that it is not possible:

i. to distinguish different types of nanoparticles, because the optical signal is averaged over all the surface area, ii. to distinguish between different states of aggregation of the nanoparticles (monomers, dimers, trimers, etc.), iii. to eliminate the unspecific signal caused by light scattered by the substrate and other potential impurities, iv. to extract fundamental spectral properties of the nanoparticles on the surface, because the optical recognition is performed with standard dark-field microscopy. Furthermore, the mechanical transduction cannot yield any information about individual nanoparticles, because only integral mechanical properties of the sensor can be measured with this platform.

SUMMARY OF THE INVENTION

The present invention provides a biosensing platform and method that solve the previously commented technical problems by simultaneously obtaining spatially and spectrally resolved information about the surface of a biosensor. Compared to the previous state of the art, with the invention described here it is possible: i) to hugely increase the signal to noise ratio of the biosensor, ii) to significantly improve the specificity of the assay, iii) to perform the simultaneous detection of multiple biomarkers (multiplexing) and iv) to achieve high-throughput suitable for diagnostic purposes. Importantly, the time required for the measurement and analysis does not depend on the number of biomarkers used in the multiplex.

The invention consists of a biosensing platform provided with a biosensor, a broadband and continuous spectrum illumination source, an optical detection system for the detection of light scattered by the biosensor, and processing means for the detected optical signal, wherein an optical detector is provided with a micrometrically dense array of spectrophotometers able to perform spatial and spectral analysis of scattered light simultaneously and an autofocus system adapted to focus the scattered signal of the biosensor's surface onto the camera. The platform is further provided with translation means for the optical detection system and/or the biosensor, such that the optical detection system and the biosensor can be displaced relative to each other in the three dimensions, and wherein the processing means are adapted to capture spatially and spectrally resolved optical signals from the sample.

The spatial and spectral information from the captured optical signals are processed such to derive the positions of scattering particles on the surface of the biosensor, and to characterize them in terms of their spectral emission. Further processing is performed to classify each of the particles, in particular, i) to determine if the particle is one of the nanoparticles used as label on the biosensor, ii) to decide to which of the labels the particle belongs in case of the simultaneous use of several labels (multiplexing), iii) to determine the state of agglomeration of the particle (monomer, dimer etc.) and iv) to discard all other particles not identified as label. For each of the labels used on the biosensor, the number of particles identified as such label is counted. From these numbers the concentrations of the biomarkers in each sample on the biosensor are quantified and presented to the user of the platform as the output result.

BRIEF DESCRIPTION OF THE DRAWINGS

To complete the description and provide for better understanding of the invention, a set of drawings is provided. Said drawings illustrate a preferred embodiment of the invention, which should not be interpreted as restricting the scope of the invention, but just as an example of how the invention can be carried out.

DESCRIPTION OF THE PREFERRED EMBODIMENTS

Figure 1:
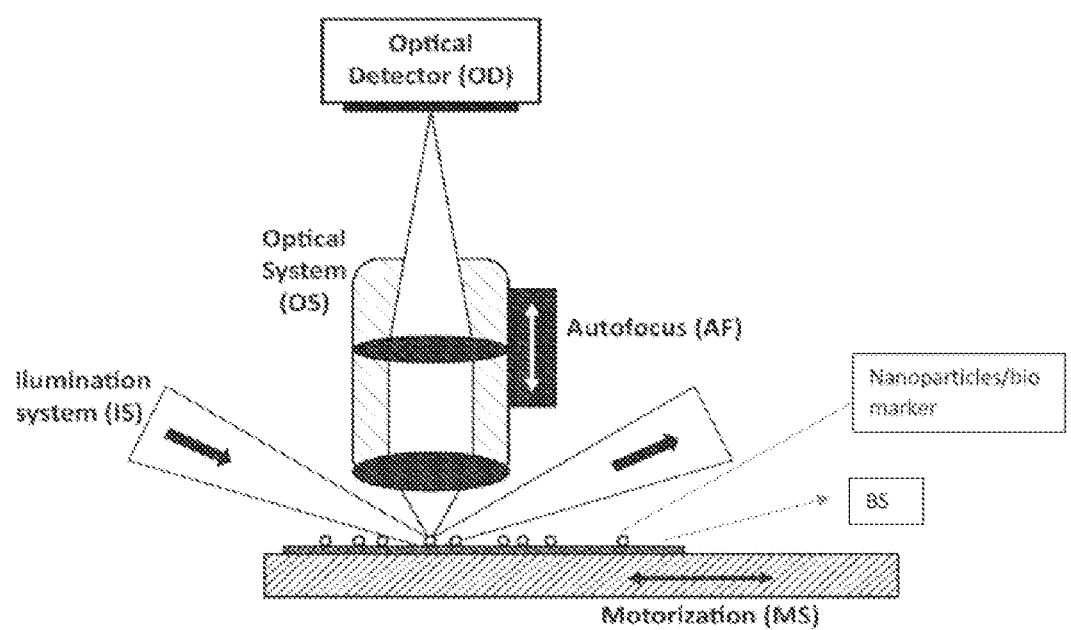
FIG. 1 is a scheme of the system according to the invention.

Referring to FIG. 1, the biosensing platform of the invention comprises:
- means to illuminate the biosensor with a broadband continuous spectrum
- means to simultaneously capture spatially and spectrally resolved optical signals from the sample, by using an optical detector with spatial and spectral resolution
- means to focus the surface from the biosensor onto the optical sensor
- means to move the biosensor and/or the optical head in the three spatial coordinates to modify their relative position.

The system comprises an optical system (OS) able to capture the scattering signal coming from the sample, an illumination system (IS) for the illumination of the sample at glazing angle, an optical detector (OD) for the simultaneous spatial and spectral analysis of the sample surface, an auto-focus unit (AF) for the fast and automatic focusing of the sample surface, and a motorization system (MS) able to produce a relative movement between the sample and the optical scanner.

Illumination System (IS)

The illumination system (IS) is composed of for example a broadband VI-NIR light source coupled to an illuminator setup. The term "broad" means that the light source presents a very broad spectral emission in the visible (400 nm-700 nm) and/or in the near infrared spectral range (from 700 nm to 1000 nm). For the purpose of the invention, a broadband light source could be a tungsten halogen lamp, a Xenon lamp, a super-continuum laser or a combination of multiple LEDs or LASERs. The illuminator setup collects the light coming from the broadband light source and illuminates the sample surface at glazing angle with a well collimated light spot.

Optical System (OS)

The main purpose of the optical system is to recover in a very efficient way the weak scattering light coming from the sample surface. The optical system (OS) in a preferential design of the invention could be an infinity-corrected optical system that is basically obtained by combining an optical objective with a tube lens. Although not optimal, the optical system (OS) could be designed with just an optical objective (finite-corrected optical system).

Figure 2:
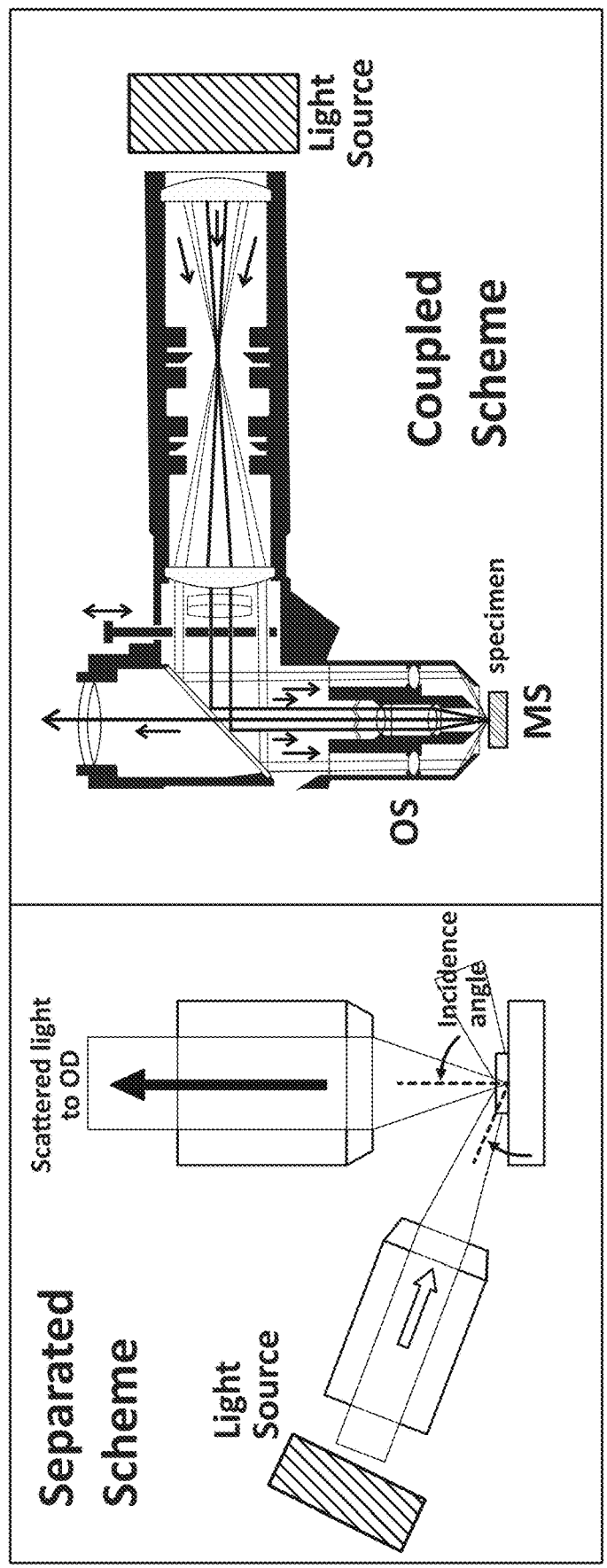
FIG. 2 shows two schemes corresponding to embodiments with separated or coupled optical and illumination systems.

The optical (OS) and the illumination (IS) systems could present separated or coupled optical paths, as shown in the schematic depiction of FIG. 2. Depending on the geometrical configuration selected (separated or coupled), the illumination system can have different geometric configurations. When the illumination system (IS) is coupled with the optical system (OS), the illumination setup could implement a Köhler or a Nelsonian illuminator. Conversely, when IS and OS have separated optical paths, the illumination system could use a glazing-angle illuminator.

In the same way, the optical system presents substantial differences depending on the geometric configuration of OS and IS to each other (coupled or separated). When the optical system (OS) is coupled with the illumination system (IS), it is necessary to implement in the optical system (OS) some elements able to separate the optical path of the illumination from the optical path of the light scattered by the sample. This condition is usually fulfilled by mounting in the optical system (OS) an optical objective and an optical beam splitter that are specifically designed for dark-field microscopy applications. Conversely, when the optical system (OS) is separated from the illumination system (IS), the optical system can be designed with standard optical elements used in bright-field applications.

Optical Detector (OD)

The optical detector captures the scattered light collected by the optical system and it has the capability to simultaneously resolve the optical signals coming from the sample surface with high spatial and spectral resolution. In order to perform spatial and spectral analysis of a sample simultaneously, it is necessary that the optical detector is a micrometrically dense array of spectrometers. The dense array gives the capability to analyze the different spatial positions of the sample simultaneously, while each spectrometer of the array allows a spectral analysis in each point of the sample. The optical detector described here allows the simultaneous analysis of a sample both in the spatial and in the spectral coordinates. The dense array of spectrometers could be realized i) with an array of photodetectors coupled with an array of optical filters arranged in a mosaic pattern, ii) with multiple arrays of photodetectors coupled with dichroic optical filters or iii) with a vertically stacked array of photodetectors able to detect different spectral bands at the same spatial position. These types of optical detectors are a viable technological solution for the simultaneous spatial and spectral analysis of a sample with sub-micrometrical resolution and at multiple spectral bands (typically at least 2 and not more than 30). Preferentially, an optical detector with a high dynamic range should be used, allowing to image nanoparticles associated with different biomarkers with only one capture, such that the time required for the measurement process does not increase in case of using more than one biomarker.

Autofocus System (AF)

To focus the sample surface in a fast and automatic way, the optical system is equipped with an autofocus system (AF); the automatic focusing of the sample can be achieved either via hardware or via software schemes. Hardware-based autofocusing systems, commonly known in literature as active autofocusing systems, are commonly obtained by projecting laser light onto the sample (the laser being part of the AF) and collecting the laser light reflected from the sample with a differential photodetector. By measuring the position of the reflected light on the photodetector, it is possible to quantify the distance of the sample surface from the best focusing position; the optimum position is therefore recovered with one or more motorized stages able to modify the relative distance between the sample and the head of the optical scanner by moving the biosensor, the optical system or part of it, or both hardware components. To precisely focus the sample surface, the typical resolution of the movement needs to be far below the depth of field of a high-resolution optical objective (which typically could reach down to 200 nm for a 100× optical objective). Many different technological solutions can be implemented, such as stepper or DC motors or piezoelectric actuators.

Software-based autofocusing systems capture several images of the sample at different relative distances between the sample and the optical head; the capture of images can be performed with the same optical detector that is used for the optical analysis of the sample, or with a dedicated one. The different captured images are analyzed with dedicated algorithms that calculate the contrast of each image and can quantify the distance of the sample surface from the best focusing position. The best position is finally recovered with one or more motorized stages able to change the relative distance between the sample and the optical head of the scanner.

Translation Means (MS)

As measurements need to be performed on very extended surface areas (thousands of $cm^2$), the system also requires the use of a motorization system able to modify the relative position between the biosensor surface and the optical system.

This task can be achieved with many different experimental configurations:

A. The sample is moved along two axes; the optical system remains stationary.

B. The optical system is moved along two axes; the sample holder remains stationary.

C. Both the optical system and the sample are moved, e.g., the optical system along one axis, and the sample holder along a second axis.

Biosensor (BS)

The biosensor comprises a functionalized substrate and functionalized nanoparticles. The target analyte is the element that will be detected from the sample, particularly from biological samples. The target analyte can be of any nature such as organic or inorganic molecules (drugs, hormones, cholesterol, etc.), biological molecules (peptides or proteins, nucleic acid molecules, growth factors, biomarkers etc.), cells (protozoan cells, bacterial cells, fungal cell, eukaryotic cells), or cell fragments (bacterial walls, cell organelles such as mitochondria, cell vesicles, etc.) or viruses.

The recognition element functionalizing the substrate surface can be any element which can recognize and bind specifically to a target analyte. In this sense, the recognition element can be an antibody (a polyclonal or monoclonal antibody), a receptor (a cell surface receptor such as an opioid receptor), a peptide (such as an opioid peptide), a protein (such as lectins), a carbohydrate (such as lipopolysaccharide O-antigen), a nucleic acid (a DNA or RNA sequence), a cell (protozoan cells, bacterial cells, fungal cell, eukaryotic cells), a microorganism or a part thereof (such as bacterial walls, cell organelles such as mitochondria, cell vesicles, etc.). In a preferred embodiment of the invention, the recognition element is an antibody, more preferably a monoclonal antibody.

The nanoparticle must naturally have plasmonic properties. In principle, any type of nanoparticle with plasmonic properties can be used. Therefore, the nanoparticle can be, for example, a gold nanoparticle, a silver nanoparticle or a nanoparticle of plasmonic metamaterial such as, but not limited to, titanium nitride and non-stoichiometric oxides such as non-stoichiometric vanadium, titanium and aluminum oxides.

Furthermore, the nanoparticle can adopt a plurality of forms or structures, such as for example, nanospheres, nanorods, pointed nanorods, nanoshells, nanocages/frames, hollow nanospheres, tetrahedra, octahedra, cubes, icosahedra, rhombic dodecahedra, concave nanocubes, tetrahexahedra, obtuse triangular bi pyramids, trisohectahedra and nanoprisms.

The nanoparticle comprises at least one detection element bound thereto which can bind specifically to the target analyte. The detection element can be any type of element which can bind to the target analyte, therefore, in principle its nature can be the same as or similar to that of the recognition element.

The function of the detection element is to detect the presence of the target analyte captured by the recognition element immobilized on the substrate surface. Therefore, the nanoparticle will only bind to the substrate by means of the detection element bound thereto if the target analyte is present in the analyzed sample. In such case, the recognition element can bind to the target analyte which is then detected by the detection element in a sandwich-type arrangement. The absence of the target analyte in the sample results in the recognition element not binding to the target analyte and therefore, detection by the detection element not occurring.

In summary, if the target analyte is present in the sample, even at ultra-low concentrations, it can be detected and quantified based on the scattering spectrum produced by each individual nanoparticle. If the target analyte is not present in the sample, there would be no detectable plasmonic effect on the substrate since nanoparticles will not be present.

Analysis of Spatially and Spectrally Resolved Information

The optical system and detector together with the translation means serve to obtain spatially and spectrally resolved information about the biosensor. This information is referred to as "images" in the following, keeping in mind that these "images" can contain much more and/or different spectral information than "typical" microscope images. The analysis of these images provides the concentrations of the biomarkers detected in each sample on the biosensor. Three aspects serve to minimize the time between image acquisition and results:

1. The main part of the analysis runs in parallel with the image acquisition.

2. Several images are analyzed in parallel, because the analysis method allows to handle the images independently for most of the analysis.

3. A highly efficient image analysis method is implemented.

Figure 3:
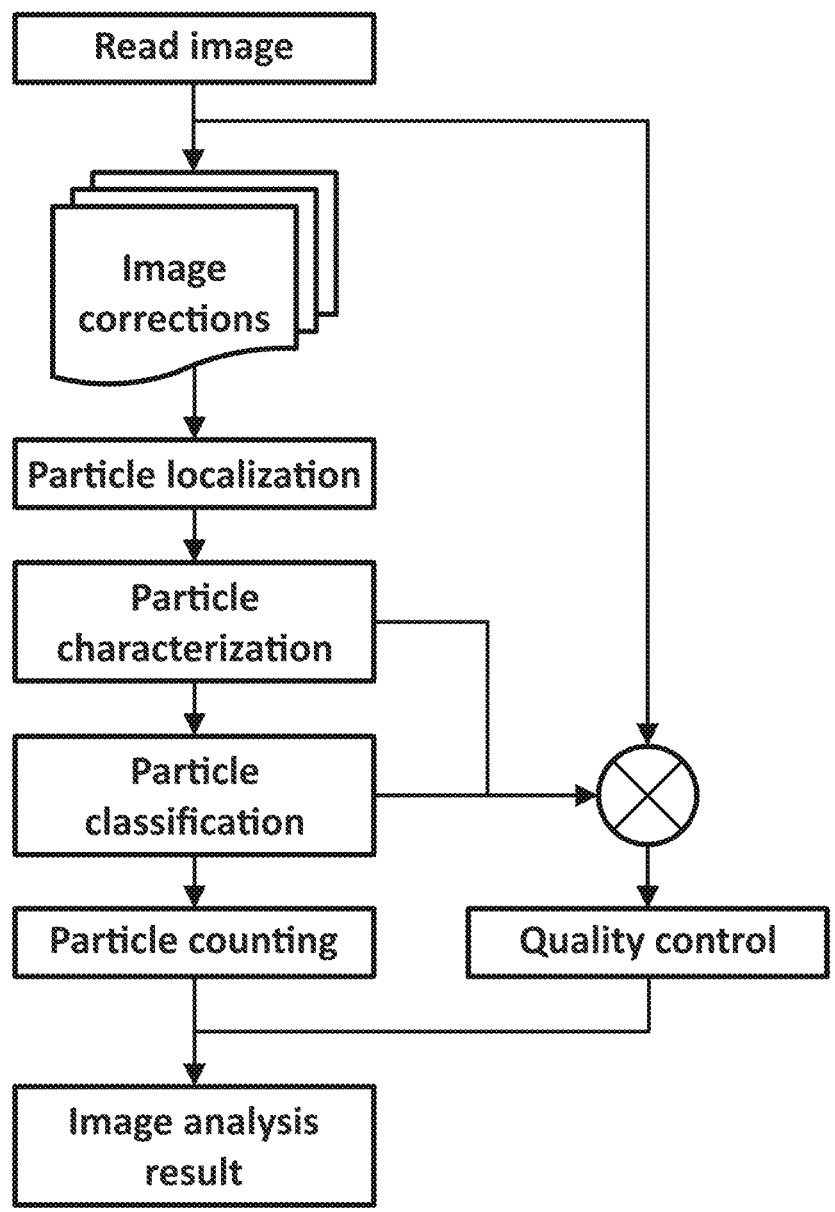
FIG. 3 is a flowchart of the method of the invention.

The core of the analysis consists in the recognition, classification and the counting of particles (see FIG. 3). Each image is read and, if needed, corrections are applied (background, inhomogeneities etc.). The particles are first localized in each analyzed image, they are characterized (brightness, emission spectrum etc.), the results are used to classify them (nano-particle monomer, cluster, dust etc.), and finally they are counted per class. These numbers constitute the principal result per image; in addition, further results are derived which allow to control the quality of the measurement (correct focusing etc.). From the numbers of the different particles in each image, the concentrations of the respective biomarkers in the corresponding sample are derived.

PREFERRED EMBODIMENTS

In a first implementation, a LED-based white-light source is used for the illumination. The light source is chosen such to cover the scattering spectrum of the particles of interest, typically from the blue (450 nm) up to the red (700 nm) for spherical gold nano-particles.

Since smaller particles scatter less light and their spectrum shifts towards the blue, preferably a light source with stronger emission in the blue-green region is chosen to (partially) compensate this effect. This compensation facilitates to image all particles with just one setting for the optical detector. To achieve a high optical resolution and an efficient light collection for the optical system, a dark-field microscope objective with a high numerical aperture (NA) is used, e.g., a 50×10.8 objective. To ensure a precise characterization and classification of the particles on the biosensor over the full field-of-view (FOV), a spherically and chromatically well corrected objective is used, e.g., a plan apochromat. An infinity-corrected objective is used to ensure flexibility in the combination with the further components of the optical system.

In a first implementation, a CCD sensor with RGB filters is used; in a second implementation, a CMOS sensor with RGB filters is used; the preferred embodiment utilizes a CMOS sensor with 16 different spectral bands arranged in a mosaic pattern. Alternatively, multiple monochromatic CCD/CMOS sensors coupled with dichroic optical filters could be implemented as optical detector, or even a sensor based on Foveon technology.

From the above, an obvious alternative to the use of a color camera or a sensor with multiple spectral bands would be the combination of a monochromatic camera with external filters (with a set of fixed filters; with a single but spectrally tunable filter etc.), or with a variable illumination (switched light sources; light source plus monochromator etc.). In all these alternatives, the camera would take one image for each filter or illumination setting, resulting in an equivalent image stack. Still, due to the necessity to take more than one image at each scan position, and to vary the filter or illumination settings between images, these alternatives are significantly slower, resulting in very low throughput inappropriate for diagnostic purposes. The advantage of the method of the invention is precisely that the required spatial and spectral information is obtained in parallel, and not sequentially, to ensure the highest possible data acquisition speed. Importantly, the optical detector used for the invention needs to perform spatial and spectral analysis of the sample surface simultaneously. The platform of this invention allows to measure an assay of about a hundred samples in a few minutes, which is at least 10-100 better than traditional micro-spectrophotometric techniques.

The geometrical dimensions of the sensor are chosen to approximately match the dimensions of the image that the optical system (i.e., the microscope objective) delivers. In standard microscopy this size would be referred to as "field number" (FN) and equal the diaphragm diameter of the eyepiece in millimeters. If the sensor is too small it does not fully utilize the available field-of-view given by the objective, if it is too large it will only be partially used. Since the aberrations of an optical system tend to increase towards the image borders, a sensor size somewhat smaller than the FN is typically the best choice to ensure a high image quality and thus a reliable detection, characterization and classification of the particles. In the current implementation, the sensor diagonal is approximately 18 mm, while the FN is 22 mm. Since the different types of nano-particles used in a multiplex typically can have very different scattering efficiencies and thus will vary significantly in brightness (e.g., by a factor of 30 or larger), a sensor with a large dynamic range is used to allow to image all particles with a single camera setting. A large dynamic range typically requires a sensor with sufficiently large image pixels, and with a low noise level.

The combination of the microscope objective and the optical detector is chosen such to allow imaging of particles smaller than 1 µm (e.g., with a diameter in the range between 50 nm and 150 nm) with an optical resolution better than 1 µm (e.g., typically between 0.5 µm and 0.9 µm), and resulting in enough pixels per particle in the image (e.g., 10 pixels per µm, referring to the object plane). Therefore, the optical detector typically has between 4 and 12 megapixels, and sizes in the order of 10×15 mm$^2$ (e.g., belonging to the so-called 1"-sensor type).

Figure 4:
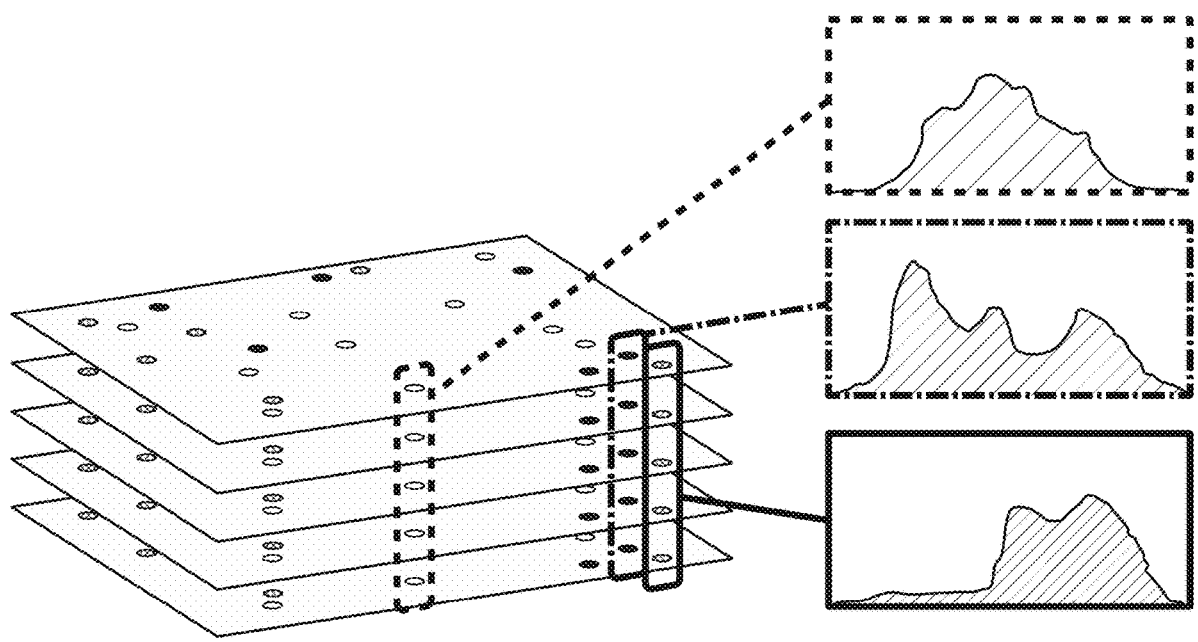
FIG. 4 shows three different spectral fingerprints for three different types of nano-particles.

In the present invention the number of spectral bands used has little influence on the image acquisition or on the data analysis; importantly, the acquired images can be arranged in order to have spatial information in two dimensions (image pixels) and spectral information in a third dimension (image layers). In an example (see FIG. 4), it is assumed that a biosensor is imaged which contains three types of nano-particles with three different spectral fingerprints. The image sensor delivers a stack of five image layers, each one corresponding to one spectral range. Using the five layers, a simplified version (only five data points) of the scattering spectra shown on the right would be obtained at each image pixel. The more spectral layers, the better the reproduction of the scattering spectra, and the easier the distinction between the spectra of different particles.

In the following, an RGB camera is used as an example to explain the image analysis method used in this invention; still, it should be understood that even if we speak of "color" or "a color component" in the following, "color" always refers to the complete spectral information from all layers available at each image pixel, and "color component" to the data from one of these layers. In the same manner, the combination of spatial and spectral information is called "image", independent of the number of spectral layers.

The parameters of the camera are adjusted to produce well-exposed images, regarding black and white level, white-balance, and color reproduction. The settings are chosen such that the nano-particles serving as biomarker labels can be well imaged, with signals above the noise level and below the saturation region (by adjusting sensitivity and exposure time) and resulting in a good discrimination between different particles in terms of the scattering spectrum ("color"; by adjusting the color-correction matrix).

Typically, the biosensor to be scanned comprises different areas corresponding to different samples, very similar to a multi-well plate, with one well per patient sample.

The spatial resolution on the biosensor is achieved with two means: the optical detector (i.e., the camera sensor) itself provides spatial resolution, and the biosensor and the optical system are moved relative to each other. In the current implementation, the biosensor is moved relative to the stationary optical system, by means of a two-axis motorized stage.

Typically, more than one image is taken of each area corresponding to the same sample, still, the images taken typically do not cover the sample area completely. In a typical scan, the number of images taken per sample and their positions within the sample area can be the same for all sample areas of the biosensor.

However, this is not necessarily the best option; the numbers and positions can also be chosen individually for each sample, e.g., such to take more images for samples which have low concentrations of biomarkers, to improve the statistical robustness of the measurement. The overall number of images which the optical platform takes during a scan of the biosensor can range from one to many thousands. The sub-division of the data acquisition in individual images has the important advantage that the analysis of those images (see corresponding chapter) can be performed in parallel to the scan, i.e., while the optical platform continues to acquire images. This permits a higher sample throughput of the platform.

The images captured during the scan are saved in a common image format, e.g., TIFF or JPEG, typically as RGB images with 8 bits per color channel. In most cases JPEG is preferred, because the resulting files are smaller and can be both written and read more rapidly. On the other hand, JPEG uses a lossy compression which especially affects the color representation. Since the spectral characterization of the particles on the biosensor is an essential aspect of this invention, only a rather mild JPEG compression is used (i.e., a high "quality factor"), to minimize potential distortions in the color representation. Alternatively:

Images can be saved with a larger color depth, e.g., as 16 bit-TIFF images, to avoid artefacts in the images in case of particles with low scattering intensities.

Images can be saved as camera raw data. This preserves the full dynamic range of the camera sensor (typically 12-14 bits), and the linear dependence between the amount of scattered light and the signal measured by the sensor.

In case of a camera with multiple spectral bands, typically the proprietary image format of the manufacturer must be used; apart from a RAW format, this can also be based on TIFF as container.

To reduce the time and the amount of memory required to store the images, and the time to analyze them, the captured images are binned. Typically, a binning of 2×2 is applied, i.e., four sensor pixels result in one image pixel. Quadratic interpolation between pixels is used to calculate the binned images. Compared to the alternative of directly using a sensor with less pixels without subsequent binning of the images, this approach achieves a better discrimination between particles in terms of color. Thus, in the current implementation image binning is applied when using a camera with 12 MP; images from 4 MP cameras are not binned, because the remaining spatial resolution would be too low.

Typically, the images are first stored locally on a hard disk of a computer or similar storage. Alternatively, the images can be directly transferred to a different computer or storage system, within the network of the platform's computer. Also, storing the images to a storage device (e.g., to a hard disk) can be omitted if, instead, the analysis of each captured image (see following paragraph) is performed directly with the image still being in the computer's memory (RAM).

For the analysis of the images from the scan, an analysis program consisting of scripts compatible with Matlab (commercially available from MathWorks) and GNU Octave (free software) could be used. Also, part or all the analysis could be implemented in hardware, e.g., using FPGAs (field-programmable gate arrays) directly connected to the optical detector. This could reduce the required analysis time. Prior to the actual analysis, the parameters of the data acquisition (the "scan") which are required for the analysis are acquired; typically, they are read from a file or database, or entered manually by the user. These parameters shall comprise the number and locations of the samples and of the individual images on the biosensor, the type(s) of biomarker(s) present in the samples, the type(s) of nano-particles and biosensor substrate used, information on the sample volumes, the illumination, and the camera and image capture settings etc. In the current implementation, this information is automatically saved in two text files during the scan; one file contains information about the settings of camera, illumination, and auto-focus, and the second one information on the geometry of the samples on the biosensor, the geometry of the images within the area of each sample, and on the samples which have actually been scanned (i.e., all samples or a subset of them). In addition, the correspondence between the samples on the biosensor and patient information (e.g., which well/sample on the biosensor corresponds to which patient ID) must have been stored; this information is not relevant for the analysis itself, but of course indispensable for the diagnostic use of its results. In a clinical environment, this information is typically stored in a central Hospital Information System (HIS). In the current embodiment, the information is edited by the person which prepares the biosensor and is stored in a folder on a network drive from which it can be read by both the platform of the invention and the analysis software.

All (or a subset of all) images acquired with the optical platform are analyzed. On the computer, this analysis can be performed strictly sequentially (one image per time) or analyzing several images in parallel (using multiple threads of the computer, e.g., one image per thread). Typically, a number of parallel threads close to the maximum available on the computer is chosen (=number of kernels, or number of logical processors), to reduce the total time of the analysis. In the current implementation, the analysis runs on the same computer which controls the data acquisition with the platform. The possibility that the information of interest on the biosensor can be obtained by analyzing different images independently is a great advantage of the technique: this way, the most time-consuming task (the analysis of each image) can be easily parallelized, and this parallelization can be scaled-up in a straight-forward, efficient, and economically feasible way (computer with more kernels, several CPUs, several computers in a network etc.). Optionally, if the images have been stored within a network, the analysis can be run on a computer different from the one which controls the platform. Likewise, the analysis of all images can be split between several computers in the network, such that each computer analyzes a subset of the images, or both the storage and the analysis could be done using a cloud service. The parallelization can be with respect to the images (one image per thread) or subdividing each image and analyzing the sub-images in parallel. The analysis can be performed after the whole biosensor has been scanned, or it can run in parallel to the scan (e.g., every time that all images of a certain sample have been taken), so that the results are obtained as quickly as possible after the scan.

During the analysis, the following steps are performed for each image: first, the image data is read from the storage (or directly from the computer's memory). Image corrections and/or transformations are then calculated, if the corresponding option has been chosen by the user, or is activated by default, or is activated automatically based on the information on the scan (type of camera sensor used, imaging parameters etc.).

A background correction of the image is performed to adjust the black level. In a typical image from the platform of the invention, the particles of interest appear as individual small bright spots on a dark background. Depending on the substrate, on the type of camera sensor, and on the acquisition parameters, this background might not appear "black" (i.e., sensor values close to zero, the "ideal" case), but "gray" (with or without a certain tint). An evaluation of the sensor values (e.g., based on a histogram of all pixels) allows to correct for both the signal offset and for a potential tint. This simplifies the characterization of the particles in a later step of the analysis.

The image is then corrected for potential inhomogeneities of the brightness. Such inhomogeneities can be due to the illumination, the light collection, the camera sensor etc. A typical effect is that the center of the image appears brighter than the borders. A correction of these effects can be necessary to ensure a correct characterization and classification of the particles in the later steps of the analysis.

A modification of the gamma curve of the image is performed to adjust the dynamical range. "Gamma curve" refers to the dependence of the pixel values in an image on the actual (physical) quantity of light detected. In standard images (JPEG, TIFF etc.), this dependence is nonlinear in such a way that with increasing light, the pixel values increase slower than proportionally. In the analysis this nonlinear dependence is corrected, using the inverse function of the "gamma curve", so that the obtained pixel values are again proportional to the amount of scattered light.

The image data is smoothed to reduce image noise. As stated before, the actual optical resolution is typically coarser than the pixel pitch on the camera sensor. This means that image noise (from the camera sensor, due to low light intensities etc.) can be reduced by smoothing without affecting the resolution. The reduction of image noise improves again the correct characterization and classification of the particles.

In case of a standard color camera, a transformation to a different color space can be performed, e.g., from RGB to HSV, L*a*b etc., which can simplify the interpretation of the results from the particle characterization and result in a more precise discrimination of particles in terms of color. The L*a*b color space, e.g., contains one channel for the light intensity (L), while the other two axes describe the color; in comparison, the channels of RGB all mix color and brightness.

If the color space used does not contain a dedicated brightness value (e.g., in RGB), such a value is calculated by summing the color channels for each image pixel. The resulting gray-scale image is referred to as "brightness image" in the following. This brightness image is typically normalized, with "0" and "1" corresponding to the lowest and highest brightness level in the given image format (8 bit-RGB: (0|0|0)→0, (255|255|255)→1).

If the color space used does not contain relative color values, such relative color contributions can be calculated, for each pixel, by dividing each color channel by the sum of the channels, e.g., $R_{rel}=R/(R+G+B)$ for the relative contribution of the channel "Red".

In case that a camera with multiple spectral bands is used, the scattering intensities measured in each of the wavelength ranges of the sensor are used instead of the RGB values. In both cases, the analysis method does not change significantly; the three values of a, e.g., RGB image are simply exchanged for an array of elements representing the different wavelength regions. The number of elements is typically larger than three to gain spectral resolution. Still, also a combination of just two well selected wavelengths can be a suitable choice for a precise discrimination between different particles.

Potential particles are then localized in the image: A gray-scale test pattern is calculated which represents the typical shape of a nano-particle in an image from the optical platform, considering the actual image acquisition parameters used (optical and sensor resolution, magnification etc.). This shape can be represented, e.g., by a two-dimensional Gaussian function, by an Airy pattern, a simple disc shape etc. In the current implementation, a sum of two Gaussian functions (G1+(−G2)) is used to approximately match the typical "donut" shaped scattering pattern of individual gold nano-particles. As a variant, instead of a single gray-scale test pattern, a pattern with colors can be used, e.g., with one pattern for each RGB component, or for each channel of a camera with multiple spectral bands. This can improve the correct identification of potential particles in the case that the shape depends on the wavelength (e.g., Gaussian shaped in the green and donut shaped in the orange spectral range).

The normalized two-dimensional cross-correlation between the brightness image and the test pattern (or patterns) is calculated. This cross-correlation image has values close to one for regions of the image which are similar in shape to the test pattern. Instead of using the brightness image, the cross-correlation can also be calculated between the test pattern and, e.g., one of the color channels of the image (or a linear combination of several channels, or some other function). This is a suitable approach if, e.g., a certain pattern is more pronounced in one channel compared to the others. A binary mask is calculated for the image. The mask equals one (=true) for pixels with a cross-correlation value above some threshold (e.g., >0.6) and a relative brightness in a certain range (e.g., >0.03 and <0.98, i.e., above noise and below saturation). All other pixels are zero (=false). Instead of a binary mask ("0" or "1"), one with continuous values can be used, e.g., a gray-scale mask with values close to one if the constraints are well matched, and close to zero if not, with all values in between possible. The given threshold values for correlation and brightness are just examples; based on the actual measurements better suited values can be selected, or thresholds on different and/or additional parameters can be chosen (color, signal-background ratio etc.). Then the binary mask is multiplied pixel-wise with the cross-correlation image. In the resulting gray scale image, the local maxima (=pixels with values higher than those of all their direct neighbors) are localized. Instead of using the product of the binary mask with the cross-correlation image, the positions of the potential particles can be derived from the binary mask only (location of the regions with value "1"). Instead of the product, other functions have been used, e.g., taking the square of the cross-correlation image etc. The positions of these local maxima are considered potential particle positions. A variant would be, instead of using the cross-correlation with a test pattern at all, to use a particle search based on thresholding techniques (e.g., everything above a certain background value is considered a potential particle), on the Hough transformation of the image (e.g., find circular objects of a certain size) etc.

An important aspect of this invention is that each particle is characterized individually; this permits the classification of the particles in the following step of the analysis.

The characterization works as follows:

a) The parameters of highest interest are the brightness and the scattering spectrum ("color") of each particle. To obtain average values of these parameters (i.e., averaged over the area of the particle), the corresponding images (brightness image, image with relative color contributions etc.) are convoluted with a suitable kernel, e.g., a two-dimensional Gaussian with a size close to the expected particle size, or with a disc-shaped pattern.

b) The resulting filtered images are evaluated at the potential particle positions calculated before.

Variant: (a.-b.) In case that the number of particles per image to be characterized is "low", it can be computationally inefficient to calculate the convolution of the whole image with a kernel to extract the mean values. Instead, it is more efficient to directly extract small regions from the image around each particle and use them to derive the mean values.—What is considered a "low" number depends on the imaging parameters, the hardware of the computer, and the implementation of the analysis routines. For a given setup, the cross-over point can be determined, such that one or the other method can be used automatically.

c) Additional characteristics of interest are the particle's size and shape, e.g., the FWHM in the brightness image, the degree of correlation with the test pattern, and the local shape at the center of the particle. The latter parameter allows to distinguish a donut shape (=indention at the center) from a Gaussian (or similar) shape (=maximum at the center). The analysis used in the current implementation uses a value which is proportional to the Discrete Laplacian at the center of the particle; this choice permits an efficient implementation based on a simple convolution of the image with a 3×3 kernel.

d) Further additional characteristics of interest are the local particle density (e.g., based on nearest neighbor distances), and further spectral characteristics (e.g., differences or ratios of spectral components).

e) As a result, the characteristics of each potential particle are obtained (their positions are already known from the previous step). For each image, this intermediate result is represented as a table, with one row for each potential particle, and as much columns as characteristics have been derived, see Table 1 for an example representing an illustration of the result from the characterization step of one image. Each row of the table corresponds to one particle, x and y are its coordinates in the image, I its brightness, and R, G, B the relative color contributions. Depending on the analysis, more columns are added for additional characterization parameters.

TABLE 1

| x | y | I | R | G | B | ... | 10 ... |
|---|---|---|---|---|---|---|---|
| 12 | 36 | 0.13 | 0.45 | 0.33 | 0.22 | | ... |
| 17 | 20 | 0.57 | 0.42 | 0.34 | 0.23 | | |
| 18 | 102 | 0.02 | 0.33 | 0.37 | 0.30 | | |
| ... | | | | | | | |

Particle Classification

Particle classification allows to consider only the particles that are most specific to the biomarker in the analysis, and is indispensable for multiplexing.

The classification works as follows:

a) If required, certain characteristics can be used to exclude particles from the further steps of the analysis. For example, if only monomers of nano-particles are of interest, and monomers show a donut shape as a distinguishing feature, this parameter can be used to eliminate all non-donut shaped particles.

b) Based on information of previous experiments, different classes of particles are defined based on their characteristics (brightness, "color", shape, size), e.g., (1) noise (very low brightness),
(2) residues from the biosensor fabrication (certain spectral pattern),
(3) dust (different spectral pattern),
(4) individual nano-particles (distinct spectral pattern, brightness, shape etc.),
(5) clusters of nano-particles (dimers, trimers etc., based on spectral pattern, brightness). For these clusters, their brightness typically depends systematically on the brightness of the corresponding individual nano-particle. This dependence is used to improve the classification.

c) In case of multiplexing (=simultaneous detection of various biomarkers, each one labelled with a different nano-particle), additional classification groups are defined to account for all nano-particles used.

d) The necessary classification parameters/rules (which combinations of characteristics correspond to each class) can be given beforehand (based on previous measurements), or can be derived from the measurement to be analyzed itself. In the second case, this analysis is typically based on the combined results from all images of a measurement, not on each one individually (to improve statistics, and to ensure that the classification is consistent among all images).

e) The classification consists basically in a segmentation of the parameter space. Its rules can be defined by the user (e.g., manual segmentation), or can be derived automatically (e.g., cluster search, k-means method, segmentation algorithms, machine learning algorithms etc.). In case of an RGB camera, an example for a classification would be that all particles with a normalized brightness in the range [>0.1, <0.7] and a relative contribution of the color channel "Red" in the range [>0.0, <0.33] are considered residues from the fabrication.

In the current implementation, the classification rules are derived as follows:

i. Two parameters from the characterization step are chosen, and a two-dimensional histogram of these two parameters from all potential particles is calculated. In case of an RGB camera, typically the normalized brightness and the relative contribution of the channel "Red" are used as parameters.

ii. In such a two-dimensional histogram, particles of the same type (e.g., individual nano-particles) will form a sort of "peak" (="dense" region of the histogram, or, in general, of the parameter space), because all of them will have similar values of brightness and color. They are similar and not identical because of differences in the individual particles, and due to noise and/or lack of precision in the measurement.

iii. In a typical measurement, the main "peak" corresponds to individual nano-particles (monomers). Based on knowledge from previous measurements, the location of this "peak" in the histogram of the data to be analyzed can be identified automatically, searching the local maximum of the histogram in a given parameter range, e.g., normalized brightness in [0.1, 0.3] and relative contribution of channel "Red" in [0.35, 0.45].

iv. Once this location of the monomers is known, the positions of dimers, trimers etc. can be estimated based on the knowledge that their brightness is approximately two times, three times etc. that of the monomers. Again, the estimates are used to guide the search for the actual local maxima.

v. The peaks of monomers, dimers etc. tend to overlap somewhat. To assign a particle to either one or the other peak, a "border" between the two peaks is defined: A routine searches for a (straight) line which best defines the "valley" in between the two peaks.

vi. The locations and separating lines between monomers, dimers, trimers, and larger agglomerations of nano-particles in the histogram are identified as described above. The rules to classify a particle as, e.g., a dimer would then be that the parameters of the particle correspond to a point in the histogram which is "to the right" (=higher normalized brightness) of the "border" separating monomers and dimers, and to the left (=lower brightness) of the "border" separating dimers and trimers. In addition, the data point must be in a certain range regarding the contribution of the channel "Red" (e.g., larger than 0.34 and smaller than 0.6).

vii. In the current implementation, the nano-particles are classified as monomers, dimers, trimers, and "larger agglomerations" (i.e., N≥4).

viii. Apart from the automatically adapted four rules for monomers, dimers, trimers, and larger agglomerations of nano-particles, fixed rules are defined for four more types of "particles":

(1) Noise: All "particles" with a normalized brightness below 0.1, and not belonging to the already defined groups of nano-particles.

(2) Residues with low brightness: "Red" below 0.33, brightness in the range [>0.1, <0.7].

(3) Residues with high brightness: "Red" below 0.33, brightness in the range [>0.7, <1.0].

(4) Saturated particles: Containing image pixels with brightness values equal to one (=saturated).

f) The classification can be manually or automatically adapted in case of differences between nano-particle lots, changes in the illumination, changes in detection parameters etc.

g) As a result, a classification of all potential particles is obtained. The representation of this result is based on the tables generated in the characterization step, adding a column with the classification result, see Table 2 for an illustration, showing the result from the classification step, for one image. Compared to Table 1, one column has been added to the right, indicating the "class" to which the corresponding particle belongs. In the example, the classes are denoted using integer numbers.

TABLE 2

| x | y | I | R | G | B | ... | ... | class |
|---|---|---|---|---|---|---|---|---|
| 12 | 36 | 0.13 | 0.45 | 0.33 | 0.22 | | | 4 |
| 17 | 20 | 0.57 | 0.42 | 0.34 | 0.23 | | | 7 |
| 18 | 102 | 0.02 | 0.33 | 0.37 | 0.30 | | | 1 |
| ... | | | | | | | | |

Particle Counting

The method described here is a "digital" technique: Instead of integrating the optical signal from the labelled biomarkers over a certain area of the biosensor, the actual number of detected labelled biomarkers is counted. This makes the method much more robust and independent from the image acquisition parameters, e.g., the brightness or the spectrum of the illumination, and from variations of the biosensor substrate, of the nano-particles etc.

The particle counting works as follows:

a) The number of particles in each classification group is counted.

b) This "counting" can be direct (one particle, one count) or weighted (e.g., with the brightness of each particle in a group, or with an estimate of the probability of a correct classification etc.).

c) As a result, the number of particles per classification group is obtained for each image. This result can be represented, e.g., as a table with one row per image, and one column for each classification group.

In case of multiplexing, it can occur that certain groups overlap significantly in the parameter space, e.g., the clusters (dimers, trimers etc.) of a less-bright nano-particle with the monomers of a different (brighter) nano-particle. In this case, the calculated numbers must be corrected:

a) Measurements in which only one type of nano-particle is present are used to calculate the ratios between monomers, dimers, trimers etc. of each type of nano-particle used in the multiplex.

b) For these particles, it is calculated which fraction of them would fall into the regions of the parameter space which belong to the further types of nano-particles used.

c) Starting, e.g., with the monomers of lowest brightness, their number is used to estimate the numbers of corresponding dimers, trimers etc., and how many of them appear in the regions of the parameter space corresponding to the other nano-particles.

d) These numbers are used to correct the number of particles counted in a certain region, i.e., the number of clusters is subtracted from the uncorrected count.

e) The procedure is repeated for the rest of the nano-particles, e.g., in order of increasing brightness.

Variant: In case of substantial overlap between the dense regions from two (or more) types of particles in the histogram, the assignment of a simple border between them might result in a significant number of wrongly classified particles. This can be reduced with an alternative approach: A suitable sum of functions is used to fit the histogram or density distribution obtained from all images, with at least one component for each particle type ("peak" in the histogram) of interest. Then, for all particles of each image (or all particles corresponding to the same sample), the weights of these components are determined which best match the histogram of this image (or sample), and these weights are used instead of the previously explained particle count.

Quality Control

To evaluate the quality of the measurement in general and of each image in particular, the area of the image in which saturation occurs is calculated (i.e., regions in which the normalized brightness is close to one), a value representative of the degree of focus of the image is derived (e.g., the mean measured size of individual nano-particles).

Apart from a general quality control, these values can be used to guide the calculation of the analysis results, see the following step.

Overall Analysis Result

In case that more than one image has been acquired for the same sample, a suitable statistical value is calculated from all images of the same sample (e.g., mean or sum of the values from the images, trimmed mean, median, quantiles etc.). In the current implementation, a trimmed mean with a symmetrical trimming of 40% is calculated from all images belonging to the same sample.

In the calculation of this value, the parameters which correlate with the quality of the images can be used to guide the selection of the most representative images of a sample, e.g., omitting those images which have too large areas in which saturation occurred (e.g., saturated area >10%), or which are not well focused (e.g., FWHM of monomers >1 µm).

For each sample, a value is calculated which correlates with the amount of biomarker present in the sample. In case of multiplexing, one such value is calculated for each biomarker. A suitable choice for this value is the number of individual nano-particles used as labels. The result can be presented as the mean number of particles per image, as a particle density (e.g., particles per $mm^2$), or as an extrapolation to the total number of particles within the sample area (an extrapolation because the images taken typically do not cover the whole area). The latter representation is preferred because it is the most direct to interpret, meaning that in a certain (known) quantity of patient sample used on the biosensor, this number of biomarkers has been detected.

The values presented to the user are provided with a suitable measure of their uncertainty, e.g., based on their standard deviation or their coefficient of variation (CV). These uncertainties can be estimated from the variations among the various images from the same sample, and/or from variations within the individual images. They can be directly reported as numbers (N±ΔN particles), and/or be used to indicate that a result is reliable or not.

If the uncertainty of the result for a sample is higher than a certain limit, the analysis software can feed back this finding to the biosensing platform. In this case, the scanner could take additional images of the corresponding sample, to verify if a consistent result can be obtained. As a further step, the analysis results could directly guide the whole scan, i.e., for each sample images are acquired until certain quality parameters are fulfilled, or an upper limit of the time or the number of images per sample is reached.

The overall result for each sample and each biomarker can be qualitative (presence or absence of the biomarker) or quantitative (concentration of the biomarker).

Proof-of-Concept Experiment, Multiplexed Spatial and Spectral Analysis of Plasmonic Nanoparticles for Biosensing Applications:

A biosensor for the detection of two biomarkers was prepared, a duplex of the two interleukins IL-6 and IL-10 (BioLegend©). A biosensor with 96 wells was used, and eight different biomarker concentrations (from 1 fg/ml to 1 ng/ml, plus a negative control) were replicated 12 times each. A Si-based multidielectric substrate of size 120 mm×80 mm was used for the biosensor. After silanization of the surface, a self-assembled monolayer based on a 1:1 mixture of the two capture antibodies for the biomarkers of interest was grown. Partitioning of the biosensor in 96 rectangular wells was achieved with a removable superstructure (GraceBio). Spherical gold nano-particles (GNPs) with diameters of 100 nm and 80 nm (NanoPartz) were functionalized with IL-6 and IL-10 detection antibodies, respectively. A 1:1 mixture of the two types of functionalized GNPs was prepared. For the samples, a buffer solution (PBST-25% FBS) was spiked with serially diluted biomarkers (1:10), resulting in final concentrations from 1 ng/ml to 1 fg/ml, plus a negative control. 200 µl of solution was used per well. The distribution of the samples is shown in Table 3; the concentrations are in units of g/ml, "0" is the negative control. Each concentration (rows 1 . . . 8) is replicated twelve times (columns 1 . . . 12).

TABLE 3

|   | 1 | 2 | . . . | . . . | 11 | 12 |
|---|---|---|---|---|---|---|
| 1 | 0 | 0 | | | 0 | 0 |
| 2 | 1 fg | 1 fg | | | 1 fg | 1 fg |
| 3 | 10 fg | 10 fg | | | 10 fg | 10 fg |
| 4 | 100 fg | 100 fg | | | 100 fg | 100 fg |
| 5 | 1 pg | 1 pg | | | 1 pg | 1 pg |
| 6 | 10 pg | 10 pg | | | 10 pg | 10 pg |
| 7 | 100 pg | 100 pg | | | 100 pg | 100 pg |
| 8 | 1 ng | 1 ng | | | 1 ng | 1 ng |

After the two incubation steps (first with the samples, then with the GNPs), the 96-well superstructure was removed. The biosensor substrate was washed several times, and finally blown dry with dry nitrogen.

In this experiment, a platform according to the invention with the following components was used:
Dark-field microscope objective 50×/0.8
Dark-field EPI illumination using a high-power white-light LED source
Camera with 12-megapixel CMOS RGB sensor
2×2 binning of images applied before storage in JPEG file format Within each well of the biosensor 13×13 images were taken. The acquisition time for the total of 16224 images was about 100 min, i.e., almost 10,000 images/hour. The high number of images was chosen to permit a detailed analysis of the homogeneity of the biosensor. For the principal result of interest, the concentrations of the two biomarkers, a much smaller number of images would have been sufficient; acquisition of, e.g., 3×3 images would have required only about 5:20 min. The magnification of the microscope objective and the size of the camera sensor result in images which correspond to a field of view of 208×284 µmt on the biosensor; with 1504×2056 pixels after binning, the image scale was 0.138 µm per pixel.

The analysis of the images was performed on the same computer which controlled the rest of the platform, in parallel to the data acquisition. Each time all 169 images of one well had been acquired, they were analyzed in parallel, using 11 threads of the computer. Since the RGB format of the images does not provide independent brightness and color values, such normalized values were calculated first:
brightness=sum of RGB values, normalized to range 0 . . . 1
relative components=each RGB component divided by the sum of the RGB values; also normalized to range 0 . . . 1.

The localization of the particles was performed as described above. A gray-scale pattern consisting of the sum of two 2-dimensional Gaussian functions was used, to match the donut shape of the emission from individual gold nanoparticles; the FWHM (full-width at half maximum) of the pattern corresponded to an apparent particle size of 0.7 µm. A correlation of at least 0.6 between pattern and image was used as acceptance criterion for a potential particle; a lower threshold of 0.03 relative brightness was set to localize even potential particles with less than 10% of the brightness of a GNP.

To obtain average values of the intensity and the emission spectrum of each particle, the previously calculated image layers (normalized brightness, normalized relative color components) were smoothed with a Gaussian filter with a sigma of 2.5 pixels, which corresponds to an averaging over an image area with a FWHM of roughly 0.8 µm, i.e., close to the typical apparent particle size. The filtered layers were evaluated at the positions obtained in the localization step, resulting in a list of characteristics for each particle (one list per image).

Figure 5:
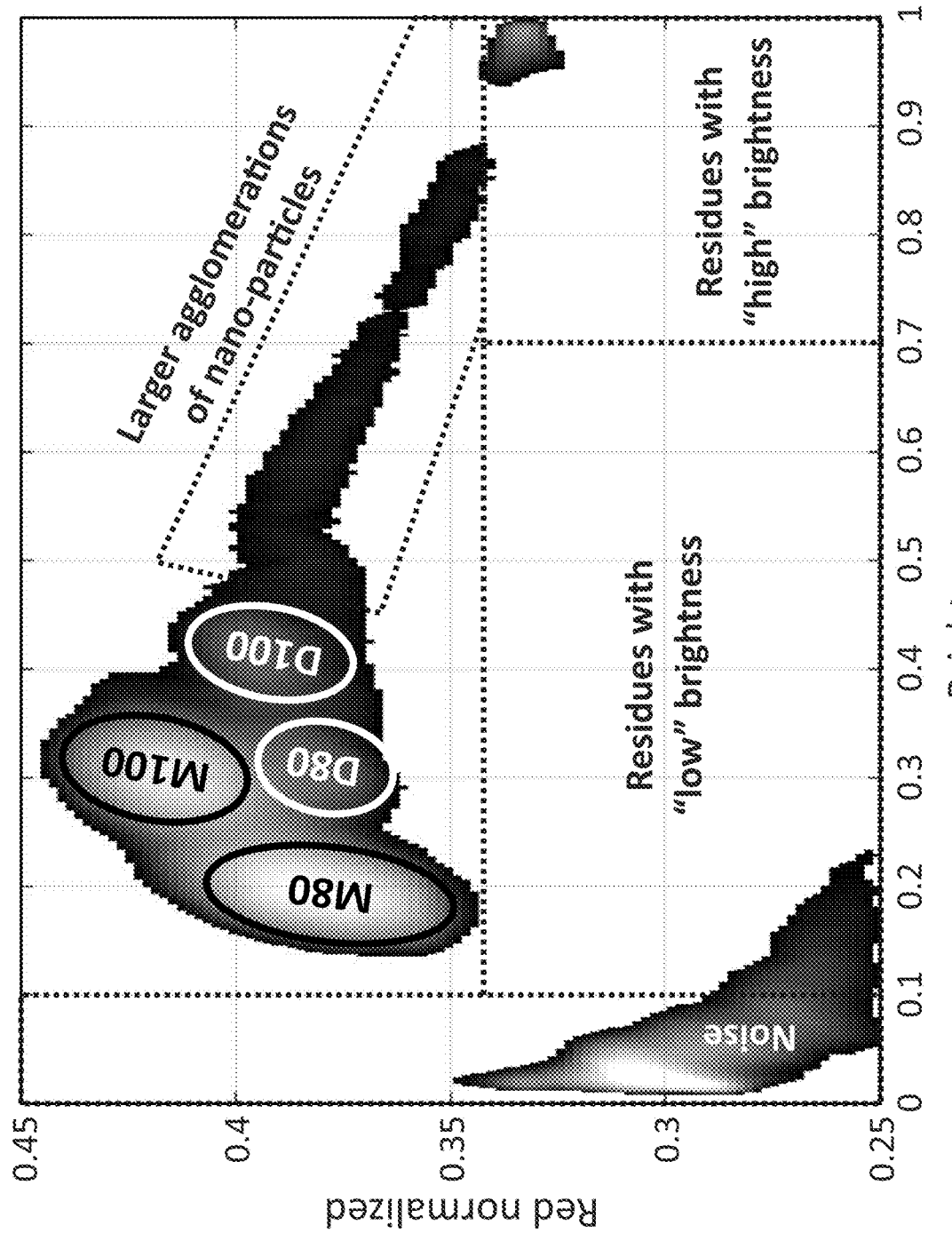
FIG. 5 is a 2-dimensional histogram of two parameter values: the normalized brightness of the particles being represented along the horizontal axis, and the relative contribution of the channel "Red" represented along the vertical axis.

From the characteristics obtained in the previous step, the normalized brightness and one color component were chosen to calculate a 2-dimensional histogram based on all particles found. The two most prominent "peaks" corresponded to the monomers of particles with 80 nm (M80) and 100 nm (M100). The corresponding dimers can also be easily distinguished (D80, D100), while the larger agglomerations overlap substantially (see FIG. 5).

At low brightness values (<0.1), the particles classified as "noise" can be seen; residues from the fabrication can be distinguished due to their different emission spectrum (<0.33); according to their brightness they are classified in two classes (0.1 ... 0.7 low; >0.7 high). Based on this histogram the classification rules are defined. The classification rules were applied to the results from the characterization step, such that the particle class was added to the already known characteristics of each particle found.

Figure 6:
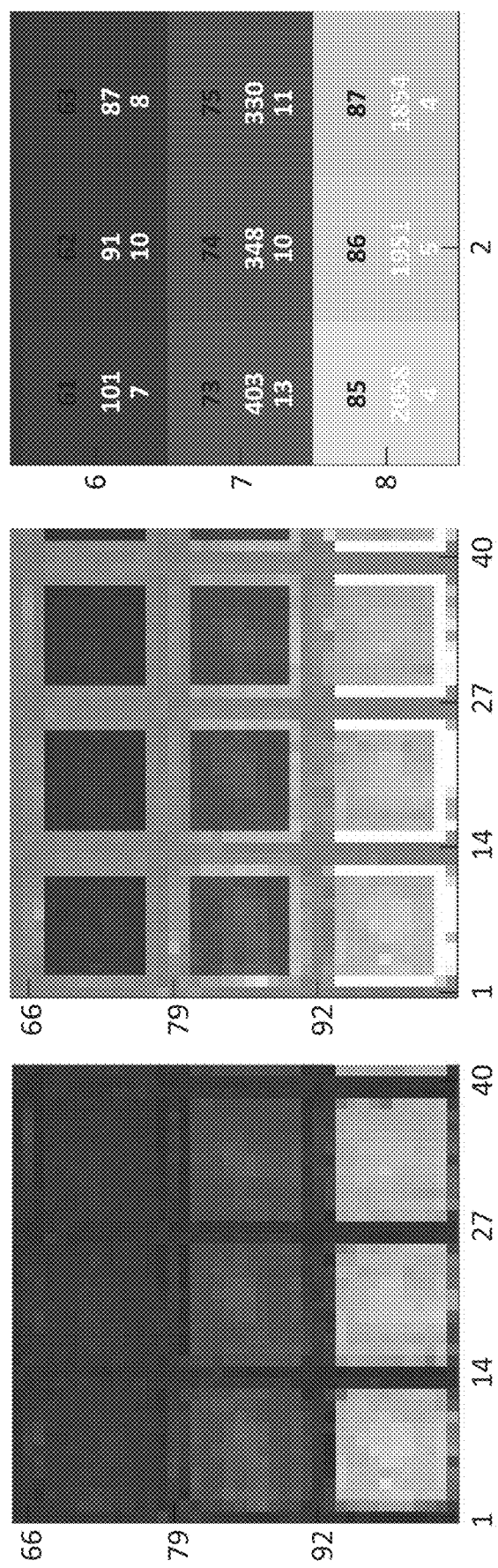
FIG. 6 shows the results for one particle class as a "heatmap", i.e., the particle numbers are gray-coded and represented in two dimensions such to resemble the positions on the biosensor.

Based on the classification obtained in the previous step, the particles within each class are counted in each image. The result can be visualized as a table with one row per image, and one column per particle class. The results per particle class are also visualized as "heatmaps", i.e., the particle numbers are shown as color-coded or gray-scale images with axes which resemble the positions on the biosensor (see FIG. 6).

Typically more than one image is taken per well to improve the counting statistics, in this experiment 13×13 images. Here, the outer two rows and columns of images of a well are within non-sensitive area of the biosensor. The remaining 9×9=81 images are within the sensitive area and are used to calculate the principal result of this well, a mean value plus its coefficient of variation (CV). In this experiment, the mean number of particles was calculated after application of a trimming of 40% to the 81 images.

Once a calibration curve has been obtained which relates the number of, e.g., monomers of one type of GNP with the concentration of the biomarker of interest in the sample, the particle counts can be converted into biomarker concentrations (see Table 4).

TABLE 4

| Sample ID (well) | IL-10 | | IL-6 | |
|---|---|---|---|---|
| | Concentration [fg/ml] | CV [%] | Concentration [fg/ml] | CV [%] |
| 1 | 112.0 | 14.6 | 54.5 | 28.0 |
| 2 | 104.5 | 14.8 | 47.3 | 22.7 |
| 3 | 111.6 | 20.4 | 46.7 | 30.7 |
| 4 | 121.2 | 16.2 | 65.5 | 30.2 |
| 5 | 142.5 | 18.9 | 79.0 | 19.2 |
| ... | ... | ... | ... | ... |
| 92 | 1800.0 | 10.0 | 974.1 | 15.5 |
| 93 | 1818.4 | 11.4 | 1017.8 | 16.3 |
| 94 | 1935.1 | 15.4 | 966.3 | 17.0 |
| 95 | 1828.6 | 9.6 | 985.9 | 17.5 |
| 96 | 1869.0 | 9.2 | 1039.4 | 13.0 |

As it is used herein, the term "comprises" and derivations thereof (such as "comprising", etc.) should not be understood in an excluding sense, that is, these terms should not be interpreted as excluding the possibility that what is described and defined may include further elements, steps, etc.

On the other hand, the invention is obviously not limited to the specific embodiment(s) described herein, but also encompasses any variations that may be considered by any person skilled in the art (for example, as regards the choice of materials, dimensions, components, configuration, etc.) to be within the general scope of the invention as defined in the claims.

The invention claimed is:

1. Biosensing platform for simultaneous, multiplexed, high throughput and ultra-sensitive optical detection of biomarkers labelled with plasmonic nanoparticles, the platform comprising a biosensor (BS), a broadband and continuous spectrum illumination system (IS), an optical detector (OD) for simultaneously capturing and resolving spatially and spectrally the scattering signal of each individual nanoparticle, an autofocus system (AF) and an optical system (OS) adapted to collect the scattered light from the biosensor's surface onto the optical detector (OD), the platform being provided with a motor for the movement of at least one of the optical system or the biosensor, such that the optical system (OS) and the biosensor (BS) can be displaced relative to each other in the three dimensions, and wherein the platform is adapted to
   (a) simultaneously capture spatially and spectrally resolved scattering signals from each nanoparticle individually and obtain spatially and spectrally resolved images from the detected biosensor's scattered signal;
   (b) correct the images to correct the black level, brightness inhomogeneities and reducing noise;
   (c) identify particles in the images and characterizing said particles at least by their color and brightness;
   (d) classify the particles;
   (e) count the particles; and
   (f) calculate the biomarker concentrations based on a previous calibration.

2. A biosensing platform according to claim 1 wherein the light source of the illumination system (IS) is a tungsten, halogen, xenon lamp or a continuum laser or a combination of multiple LEDs or LASERs in the visible and near-infrared spectral range.

3. A biosensing platform according to claim 1 wherein the optical system (OS) includes a microscope objective.

4. A biosensing platform according to claim 1 wherein the optical system (OS) includes an infinity-corrected optical system combined with a tube lens.

5. A biosensing platform according to claim 1 wherein the auto focus system (AF) is implemented as a computer program.

6. A biosensing platform according to claim 1 wherein the optical detector (OD) is; a dense array of multiple monochromatic CMOS or CCD sensors coupled with dichroic optical filters, or a vertically stacked array of photodetectors able to detect different spectral bands at the same spatial position.

7. A biosensing platform according to claim 1 wherein the optical detector (OD) is a CMOS or a CCD sensor coupled with an array of optical filters arranged in a mosaic pattern.

8. A biosensing platform according to claim 7 wherein the optical filters are RGB filters.

* * * * *